(12) United States Patent
Govari et al.

(10) Patent No.: US 12,016,728 B2
(45) Date of Patent: Jun. 25, 2024

(54) ESTIMATING STRAIN ON TISSUE USING 4D ULTRASOUND CATHETER

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) LTD. (IL)

( * ) Notice: Subject to any disclaimer, the term of this patent is extended or adjusted under 35 U.S.C. 154(b) by 0 days.

(21) Appl. No.: 17/357,267

(22) Filed: Jun. 24, 2021

(65) Prior Publication Data

US 2022/0409180 A1 Dec. 29, 2022

(51) Int. Cl.
*A61B 8/08* (2006.01)
*A61B 8/00* (2006.01)
(Continued)

(52) U.S. Cl.
CPC ............... *A61B 8/485* (2013.01); *A61B 8/02* (2013.01); *A61B 8/12* (2013.01); *A61B 8/4245* (2013.01); *A61B 8/4494* (2013.01)

(58) Field of Classification Search
CPC .. A61B 8/485; A61B 8/02; A61B 8/12; A61B 8/4245; A61B 8/4494; A61B 5/367; A61B 5/343; A61B 8/0833
See application file for complete search history.

(56) References Cited

U.S. PATENT DOCUMENTS 6,332,089 B1 12/2001 Acker et al.
6,527,717 B1 3/2003 Jackson et al.
(Continued)

FOREIGN PATENT DOCUMENTS

| WO | WO9605768 | 2/1996 | |
| WO | WO2020/044117 | 3/2020 | |
| WO | WO-2020206432 A1 * | 10/2020 | ......... A61B 18/1492 |

OTHER PUBLICATIONS

Hess, Aaron T., et al. "Myocardial 3D strain calculation by combining cine displacement encoding with stimulated echoes (DENSE) and cine strain encoding (SENC) imaging." Magnetic Resonance in Medicine: An Official Journal of the International Society for Magnetic Resonance in Medicine 62.1: 77-84 (Year: 2009).*

(Continued)

*Primary Examiner* — Colin T. Sakamoto
*Assistant Examiner* — Tommy T Ly

(57) ABSTRACT

A medical system includes an ultrasound probe configured for insertion into an organ of a body, and a processor. The probe includes a two-dimensional (2D) ultrasound transducer array, and a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) estimate, based on the ultrasound images acquired over the given time duration, three-dimensional displacements as a function of time for one or more locations in the tissue region, (c) estimate respective mechanical strains of the one or more locations in the tissue region, based on the three-dimensional displacements, and (d) present a time-dependent rendering of the mechanical strains to a user.

14 Claims, 3 Drawing Sheets

(51) Int. Cl.
    *A61B 8/02*    (2006.01)
    *A61B 8/12*    (2006.01)

(56) References Cited

U.S. PATENT DOCUMENTS

| | | | |
|---|---|---|---|
| 6,618,612 B1 | 9/2003 | Acker et al. | |
| 7,542,544 B2 | 6/2009 | Rubin et al. | |
| 8,858,441 B2* | 10/2014 | Konofagou | G01S 15/8956 600/443 |
| 9,980,786 B2 | 5/2018 | Saul et al. | |
| 10,537,306 B2 | 1/2020 | Schaer et al. | |
| 2002/0065455 A1 | 5/2002 | Ben-Haim et al. | |
| 2003/0120150 A1 | 6/2003 | Govari | |
| 2003/0158483 A1* | 8/2003 | Jackson | A61B 8/0883 600/449 |
| 2004/0034304 A1* | 2/2004 | Sumi | G01S 7/52042 600/439 |
| 2004/0068178 A1 | 4/2004 | Govari | |
| 2008/0300487 A1* | 12/2008 | Govari | A61B 34/20 600/443 |
| 2012/0172867 A1* | 7/2012 | Ryu | A61B 34/20 606/41 |
| 2015/0289840 A1* | 10/2015 | Konofagou | A61B 8/485 600/438 |
| 2016/0249880 A1* | 9/2016 | Konofagou | G16H 50/30 600/438 |
| 2017/0020486 A1 | 1/2017 | Salcudean et al. | |
| 2020/0061340 A1 | 2/2020 | Mixter et al. | |
| 2020/0163646 A1* | 5/2020 | Konofagou | A61B 8/485 |
| 2020/0214662 A1* | 7/2020 | Konofagou | A61B 5/339 |
| 2021/0169394 A1* | 6/2021 | Chou | A61B 34/10 |
| 2021/0308490 A1* | 10/2021 | Hu | G01P 13/00 |
| 2022/0192640 A1* | 6/2022 | Vignon | A61B 8/0883 |

OTHER PUBLICATIONS

Bunting, Ethan, et al. "Cardiac lesion mapping in vivo using intracardiac myocardial elastography." IEEE transactions on ultrasonics, ferroelectrics, and frequency control 65.1 (2017): 14-20.

Grondin, et al. "4D cardiac electromechanical activation imaging," Computers in biology and medicine, 113 (2019): 103382.

Wildes, D. et al., "4D ICE: A 2D Array Transducer With Integrated ASIC in a 10-Fr Catheter for Real-Time 3D Intracardiac Echocardiography," in IEEE Transactions on Ultrasonics, Ferroelectrics, and Frequency Control, vol. 63, No. 12, pp. 2159-2173, Dec. 2016, doi: 0.1109/TUFFC.2016.2615602.

Satoshi, Yuda et al., "inter-Vendor Variability of Left Ventricular Volumes and Strains Determined by Three-Dimensional Speckle Tracking Echocardiography", Echocardiography, Futura Publishing Co., Amonk, NY, US, vol. 31, No. 5, Nov. 6, 2013, pp. 597-604.

Extended European Search Report dated Nov. 21, 2022 from corresponding EP Application No. 22180644.1-1126.

* cited by examiner

ESTIMATING STRAIN ON TISSUE USING 4D ULTRASOUND CATHETER

FIELD OF THE INVENTION

The present invention relates generally to invasive medical instruments and methods, and particularly to intra-body medical probes and methods employing ultrasound.

BACKGROUND OF THE INVENTION

Invasive ultrasound techniques to assess dynamic properties of wall tissue of organs within the body have been previously proposed. For example, Bunting, et al. describe a strain-based method called Myocardial Elastography (ME), for characterizing the size and location of ablation lesions within the myocardium, in a paper titled "Cardiac lesion mapping in vivo using intracardiac myocardial elastography," IEEE transactions on ultrasonics, ferroelectrics, and frequency control, 65.1 (2017), pages 14-20.

As another example, U.S. Pat. No. 6,527,717 describes accurate tissue motion systems and methods. Motion of the ultrasound transducer is accounted for in estimates at tissue motion. In one embodiment, a motion sensor comprises a position sensor for determining a location of a transducer relative to the target or other reference points. The motion sensor may comprise a magnetic or electromagnetic position sensor. Correcting for transducer motion better isolates localized tissue contractions or expansions, such as motion of the myocardial muscle or fibers. Accurate motion estimation is also provided by determining an angle of motion from the ultrasound data. The angle of motion is used to adjust velocity estimates, providing two-dimensional velocity vectors (i.e., motion estimates comprising motion in at least two dimensions). Movement of tissue is determined by correlating speckle or a feature represented by two different sets of ultrasound data obtained at different times. Additional aspects include tracking the location of a tissue of interest. A characteristic of strain, such as the strain rate or strain is calculated for the tracked tissue of interest. Ultrasound data associated with different positions relative to the transducer are selected as a function of the tracking and used to determine the characteristic of strain. Motion estimates corrected for transducer motion may also be used to determine a strain or strain rate. In yet another aspect, motion estimates are generated with data from an intra-cardiac transducer array. The characteristic of strain is determined from the motion estimates. Other aspects discussed above may be used with an intra-cardiac transducer array, providing accurate motion analysis based on imaging from within the heart.

In a paper titled "4D cardiac electromechanical activation imaging," Computers in biology and medicine, 113 (2019): 103382, Grondin, et al. suggest a possibility that electromechanics wave imaging technique could enable scientists to link the electrical and mechanical functions of the heart. Such linking capability is of high clinical value because cardiac diseases typically manifest themselves in both electrical and mechanical aspects, but is currently absent given the dearth of such mapping techniques in vivo.

U.S. Patent Application Publication 2020/0214662 describes systems and methods for generating an electromechanical map. The methods include obtaining ultrasound data comprising a series of consecutive image frames and radio frequency (RF) signals corresponding to the location in the heart; measuring displacements and strains based on the ultrasound data to determine an electromechanical activation in the location; converting the ultrasound data into a series of isochrone maps; and combining the series of isochrone maps to generate the electromechanical map. The electromechanical map illustrates the electromechanical activation and internal wall structures of the heart.

U.S. Pat. No. 7,542,544 describes an ultrasonic imaging system that acquires echo signals from an object being imaged such as a moving coronary artery and the cross-correlation between echo signals is employed as an objective measure of relative object location. The method is used in a pre-scan procedure to determine an optimal gating window to acquire image data during a cardiac gated scan, and it is used during the scan as a real time gating signal. The invention enables a very flexible gating scheme. Since the acquired correlation data indicates the instant-to-instant correlation of any phase of the heart cycle to any other phase, it is possible to gate during any phase of the cycle if one desires to do so. It just requires more heart beats to acquire the data. It is also possible to acquire image data if the patient has an arrhythmia, since beat-to-beat mapping can be accomplished for any spatial correspondence including correspondences that change between beats. Finally, the correlation detects any changes with respiration, so multiple breath holds can also be accommodated.

PCT International Publication WO 2020/044117 describes a catheter-based ultrasound imaging system configured to provide a full circumferential 360-degree view around an intra-vascular/intra-cardiac imaging-catheter-head by generating a three-dimensional view of the tissue surrounding the imaging-head over time. The ultrasound imaging system can also provide tissue-state mapping capability. The evaluation of the vasculature and tissue characteristics include path and depth of lesions during cardiac-interventions such as ablation. The ultrasound imaging system comprises a catheter with a static or rotating sensor array tip supporting continuous circumferential rotation around its axis, connected to an ultrasound module and respective processing machinery allowing ultrafast imaging and a rotary motor that translates radial movements around a longitudinal catheter axis through a rotary torque transmitting part to rotate the sensor array-tip. This allows the capture and reconstruction of information of the vasculature including tissue structure around the catheter tip for generation of the three-dimensional view over time.

However, known approaches of measuring strain upon a tissue in vivo are often noisy or do not provide the desired visibility to enable desired clinical uses. Accordingly, improvements are desired.

SUMMARY OF THE INVENTION

An embodiment of the present invention that is described hereinafter provides a medical system including an ultrasound probe and a processor. The ultrasound probe is configured for insertion into an organ of a body, the ultrasound probe including (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) estimate, based on the ultrasound images acquired over the given time duration, three-dimensional displacements as a function of time for one or more locations in the tissue region, (c) estimate respective mechanical strains of the one or more locations in the tissue region, based on the three-dimensional displacements, and (d) present a time-dependent rendering of the mechanical strains to a user.

In some embodiments, the processor is configured to present the time-dependent rendering of the mechanical strains together with an electrophysiological (EP) signal layer.

In some embodiments, the EP signal layer includes local activation times (LAT). In other embodiments, the EP signal layer includes one of bipolar tissue-voltage levels and unipolar tissue-voltage levels.

In an embodiment, the processor is configured to generate, using the signals output by the sensor, a composite rendering including a layer of timing of heart beats and a layer of local activation times (LAT).

In another embodiment, the processor is further configured to identify scar tissue in the tissue region using the estimated strains.

There is additionally provided, in accordance with another embodiment of the present invention, a medical system including an ultrasound probe and a processor. The ultrasound probe is configured for insertion into an organ of a body, the ultrasound probe including (i) a two-dimensional (2D) ultrasound transducer array, and (ii) a sensor configured to output signals indicative of a position, direction and orientation of the 2D ultrasound transducer array inside the organ. The processor is configured to (a) using the signals output by the sensor, register multiple ultrasound images of a tissue region, acquired over a given time duration by the 2D ultrasound transducer array, with one another, (b) estimate, based on the ultrasound images acquired over the given time duration, three-dimensional displacements as a function of time for one or more locations in the tissue region, (c) estimate respective mechanical strains of the one or more locations in the tissue region, based on the three-dimensional displacements, and (d) estimate, based on the strains, a parameter of a cardiac cycle in the region.

In some embodiments, the processor is configured to visualize the parameter of the cardiac cycle to a user.

In some embodiments, the processor is configured to generate, using the signals output by the sensor, a composite rendering including the estimated parameter of the cardiac cycle and an electrophysiological (EP) signal layer.

In an embodiment, the parameter of the cardiac cycle includes a cycle length. In another embodiment, the parameter of the cardiac cycle includes a timing of the cardiac cycle.

In some embodiments, the processor is configured to trigger another device synchronously with the cardiac cycle using the detected timing.

There is further provided, in accordance with another embodiment of the present invention, a method including inserting an ultrasound probe into an organ of a body, the ultrasound probe including (i) a two-dimensional (2D) ultrasound transducer array, and (ii) a sensor configured to output signals indicative of a position, direction and orientation of the 2D ultrasound transducer array inside the organ. Using the signals output by the sensor, multiple ultrasound images of a tissue region are registered with one another, that were acquired over a given time duration by the 2D ultrasound transducer array. Based on the ultrasound images acquired over the given time duration, three-dimensional displacements as a function of time are estimated for one or more locations in the tissue region. Respective mechanical strains of the one or more locations in the tissue region are estimated based on the three-dimensional displacements. A time-dependent rendering of the mechanical strains is presented to a user.

There is furthermore provided, in accordance with another embodiment of the present invention, a method including inserting an ultrasound probe into an organ of a body, the ultrasound probe including (i) a two-dimensional (2D) ultrasound transducer array, and (ii) a sensor configured to output signals indicative of a position, direction and orientation of the 2D ultrasound transducer array inside the organ. Using the signals output by the sensor, multiple ultrasound images of a tissue region are registered with one another, that were acquired over a given time duration by the 2D ultrasound transducer array. Based on the ultrasound images acquired over the given time duration, three-dimensional displacements as a function of time are estimated for one or more locations in the tissue region. Respective mechanical strains of the one or more locations in the tissue region are estimated based on the three-dimensional displacements. Based on the strains, a parameter of a cardiac cycle is estimated in the region.

The present invention will be more fully understood from the following detailed description of the embodiments thereof, taken together with the drawings in which:

DETAILED DESCRIPTION OF EMBODIMENTS

Overview

Figure 1:
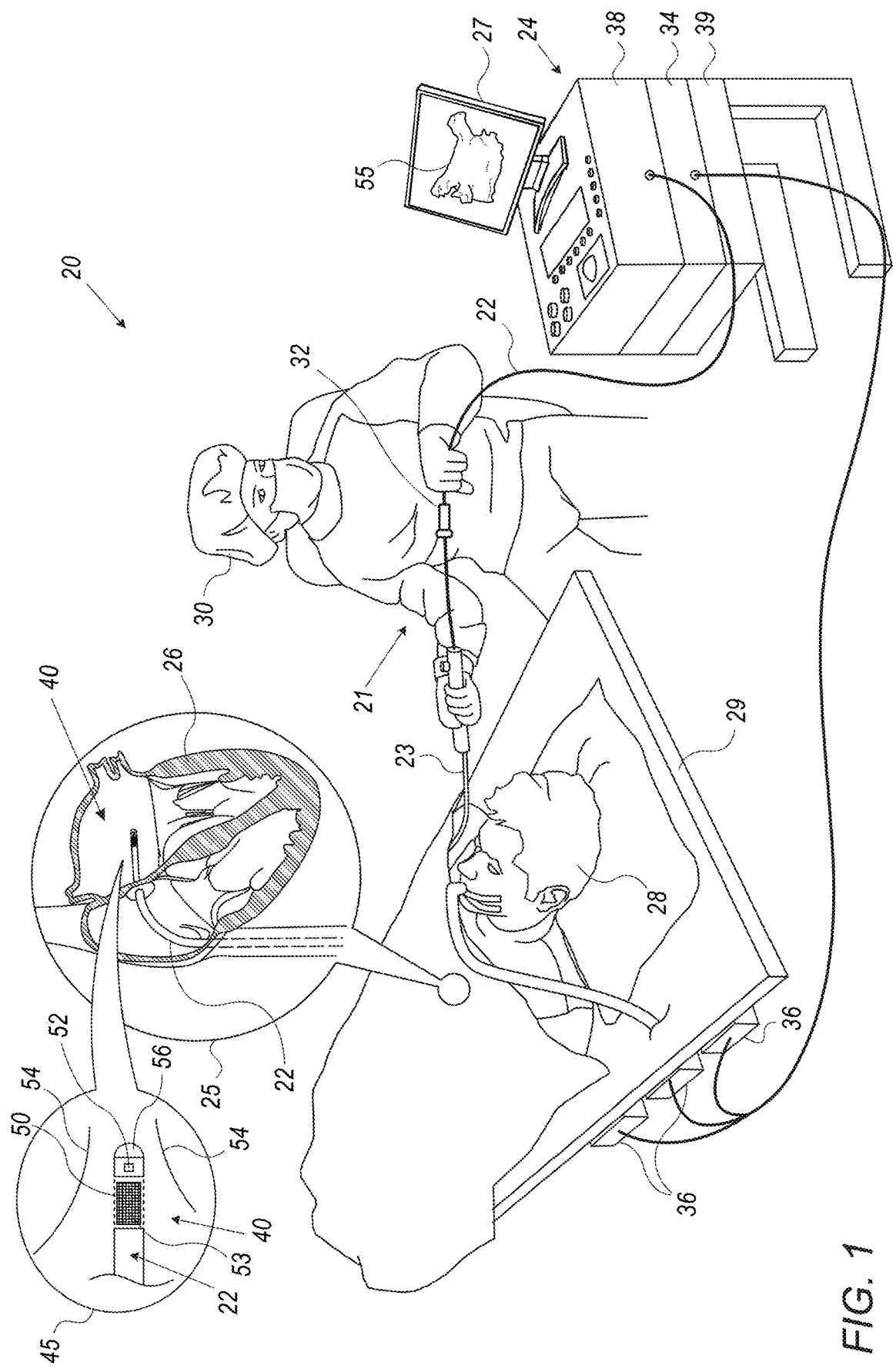
FIG. 1 is a schematic, pictorial illustration of a catheter-based ultrasound imaging system using a catheter with a distal end assembly comprising a 2D ultrasound probe and a location sensor, in accordance with an embodiment of the present invention.

Embodiments of the present invention that are described herein provide methods and systems that use a probe, such as a catheter, having a two-dimensional (2D) array of ultrasound transducers, for producing three-dimensional (3D) or four-dimensional (4D) ultrasound images. In the present context, the term "3D ultrasound image" refers to an ultrasound image that represents a certain volume in three dimensions. The term "4D ultrasound catheter" refers to a catheter incorporating a 2D array of ultrasound transducers. The term "4D ultrasound image" refers to a time-series of 3D ultrasound images of a certain volume acquired by the 2D array. A 4D image can be regarded as a 3D movie, the fourth dimension being time. Another way of describing 4D image (or rendering) is as a time-dependent 3D image (or rendering). Where used in the heart, a 4D ultrasound catheter may be referred to as "4D Intracardiac Echocardiography (ICE)" catheter.

In the disclosed embodiments, the catheter also comprises an integral location sensor, such as a magnetic position sensor, that is pre-registered with the 2D array based on the known relative position and orientation on the catheter shaft between the location sensor and the 2D array. The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber. Because of the integral location sensor, and its pre-registration with the 2D array, the spatial coordinates of every voxel in the imaged section are known.

In one embodiment, a processor registers the real-time acquisitions (e.g., images of a given cardiac region acquired over a given time duration) in space, with one another, using the location data from the location sensor. In this manner the processor can subtract catheter motion and therefore show tissue region motion with very high accuracy. The method may be applied at the acquired data level or at an image level, where images are registered to remove catheter motion.

In particular, some embodiments of the present invention use a 4D ultrasound catheter to measure motion of a selected tissue region with high spatiotemporal resolution. The motion analysis may be performed by an algorithm which tracks tissue locations in a sequence of images such as in a sequence of an MPEG images. The operator of the 4D catheter can select a particular tissue location, $(\xi, \eta, \zeta)$, for example in the wall of the left ventricle. A processor then tracks the tissue location in three dimensions over time. The tracking provides 3D values of tissue location displacements $(\Delta\xi, \Delta\eta, \Delta\zeta)$ over time, and the different values correspond to the mechanical strain of the tissue therein.

As indicated above, the accuracy of the values of displacements $(\Delta\xi, \Delta\eta, \Delta\zeta)$ is significantly greater than for catheters without an integral location sensor, since the latter do not have any way of subtracting out their own motion. Furthermore, because the strain is measured in three orthogonal directions, embodiments of the invention can calculate a strain tensor, as described below. The results provide precise cardiac motion in three dimensions that the processor can present to a user as a map or a video.

Typically, electrophysiological (EP) renderings of heart chamber images presented to an electrophysiologist are tissue surface maps, overlaid with color values of a derived electrical parameter, such as the local activation time (LAT). The flow of the cardiac EP wavefront over a chamber, such as a ventricle, as the heart beats, provides useful information to the electrophysiologist. The LAT typically corresponds to motion of the heart muscle, and it would be useful to be able to visualize this motion without having to acquire the electrical signals used to derive the LAT. It would also be useful to correlate EP parameter flow with movement of the heart muscle along the cardiac cycle.

Some embodiments of the present invention use the 4D ultrasound catheter to acquire images of the heart chamber walls during a given heartbeat. The images are analyzed to show how the muscle moves in a wave through the heart during the heartbeat. In an embodiment, the processor converts the amount of movement into a color scale, and then overlays the colors indicative of the movement on the ultrasound image. The resulting image effectively acts as a replacement for the "standard" LAT map, but has the advantage of not requiring acquisition of electrical signals from the heart.

Alternatively, the wave movement may be incorporated into the EP parameter map, so that both the EP propagation ("electrical motion") and the physical motion may be observed on the same map at the same time. By having the two motions visualized on the same map, the correlation between them (or an absence of correlation, which may indicate a tissue source of rhythm disorder) can be observed.

If a heart is beating irregularly, i.e., it is not in sinus rhythm, it may be difficult to measure the rate of beating, i.e., the cycle length. Some embodiments of the present invention, therefore, use the 4D ultrasound catheter to acquire images of the heart chamber walls as the heart beats. In an embodiment, the images are acquired over a number of heartbeats and the images are analyzed to show muscle movement of the heart. These movements are then used to estimate parameters of the cardiac cycle, e.g., the cycle length and the timing of the cycle relative to some reference time.

The analysis may also show details of any irregularity, such as atrial fibrillation (AF) or premature ventricular contraction (PVC), that may be occurring. The cycle length and the timing may be correlated with measured electrical activity, e.g., electrocardiograph (ECG) signals, so that the acquired ultrasound images may be used as a trigger to some external device, instead of using ECG signals.

During an intracardiac procedure involving ultrasound imaging, it is sometimes difficult to identify regions of a chamber comprising scar tissue. Some embodiments of the invention image a wall of the heart, such as the wall of the left ventricle, and measure movement of the surface of the wall. Scarred areas of the wall move differently from surrounding areas, and typically do not move at all. In some embodiments, the processor analyzes the acquired images, in real time, to identify stationary areas or areas which move differently from their surroundings. The identified areas are marked as scar tissue, also in real time, on the displayed video image.

System Description

FIG. 1 is a schematic, pictorial illustration of a catheter-based ultrasound imaging system 20 using a catheter 21 with a distal end assembly 40 comprising a 2D ultrasound-array 50 and a location sensor 52, in accordance with an embodiment of the present invention. Integral location sensor 52 is pre-registered with the 2D array 50 of catheter 21.

Specifically, sensor 52 is configured to output signals indicative of a position and orientation of the 2D ultrasound transducer array 52 inside the organ. A processor of the system is configured to, using the signals output by the sensor, register multiple ultrasound image sections, acquired by the 2D ultrasound transducer array 50, with one another.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the embodiment described herein, catheter 21 is used for ultrasound-based diagnostic purposes, although the catheter may be further used to perform a therapy such as electrical sensing and/or ablation of tissue in heart 26, using, for example, a tip electrode 56.

Physician 30 navigates distal end assembly 40 of catheter 21 to a target location in heart 26 by manipulating shaft 22 using a manipulator 32 near the proximal end of the catheter.

In an embodiment, 2D ultrasound-array 50 shown in detail in an inset 25, is configured to image a left atrium of heart 26.

As seen in an inset 45, ultrasound-array 50 comprises a 2D array 50 of multiple ultrasound transducers 53. Inset 45 shows ultrasound-array 50 navigated to an ostium 54 of a pulmonary vein of the left atrium. In this embodiment, 2D array 50 is an array of 32×64 ultrasound transducers. The 2D array is able to image a section of the inner wall of the ostium. Because of the integral location sensor, and its preregistration with the 2D array, the spatial coordinates of every pixel in the imaged section are known. An example of a suitable 2D array is described in D. Wildes et al., "4-D ICE: A 2-D Array Transducer With Integrated ASIC in a 10-Fr Catheter for Real-Time 3-D Intracardiac Echocardiography," in IEEE Transactions on Ultrasonics, Ferroelectrics, and Frequency Control, vol. 63, no. 12, pp. 2159-2173, December 2016, doi: 10.1109/TUFFC.2016.2615602, which is incorporated herein by reference in its entirety.

Control console 24 comprises a processor 39, typically a general-purpose computer, with suitable front end and interface circuits 38 for receiving signals from catheter 21, as well as for, optionally, applying treatment via catheter 21 in heart 26 and for controlling the other components of system 20. Console 24 also comprises a driver circuit 34, configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

Exemplary catheters and imaging assemblies that enable deflection and rotation to facilitate imaging by the physician are described in detail in U.S. Pat. Nos. 9,980,786; 10,537, 306; and U.S. Patent Publication No. 2020-0061340 A1, whose disclosures are all incorporated herein by reference.

In some embodiments, processor 39 may be configured to operate array 50 in a "temporal mode" to image motion in time of a cardiac region, with gated acquisition occurring over a number of heartbeats. Additionally, or alternatively, the imaging may be done over a single heartbeat. In an embodiment, the imaged cardiac region is presented to physician 30 by processor 39 on a monitor 27, e.g., as a real-time volume rendering 55 video.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations.

Estimating and Presenting Strain on Tissue

As noted above, the operator of the 4D catheter can select a particular tissue location $(\xi, \eta, \zeta)$, for example in the wall of the left ventricle, and the tissue location is tracked in three dimensions over time. The tracking provides 3D values of tissue location changes $(\Delta\xi, \Delta\eta, \Delta\zeta)$ over time, and the different values correspond to the strain of the tissue therein.

A 3D strain tensor, that can be subsequently visualized over organ rendering, may be calculated as follows:

$$E = \tfrac{1}{2}(F^T F - I) \qquad \text{Eq. 1}$$

where I is the identity matrix, and F is the tissue deformation gradient tensor that is given by:

$$F = \begin{pmatrix} \frac{\partial \xi}{\partial x} & \frac{\partial \xi}{\partial y} & \frac{\partial \xi}{\partial z} \\ \frac{\partial \eta}{\partial x} & \frac{\partial \eta}{\partial y} & \frac{\partial \eta}{\partial z} \\ \frac{\partial \zeta}{\partial x} & \frac{\partial \zeta}{\partial y} & \frac{\partial \zeta}{\partial z} \end{pmatrix} \qquad \text{Eq. 2}$$

where $\xi$, $\eta$ and $\zeta$ represent components at the measurement time and x, y, and z represent mutually orthogonal components at the reference time, as noted in our coordinate system. The deformation gradient tensor depicts the change in each axis of a unit vector from the reference time to the time of measurement.

Figure 2:
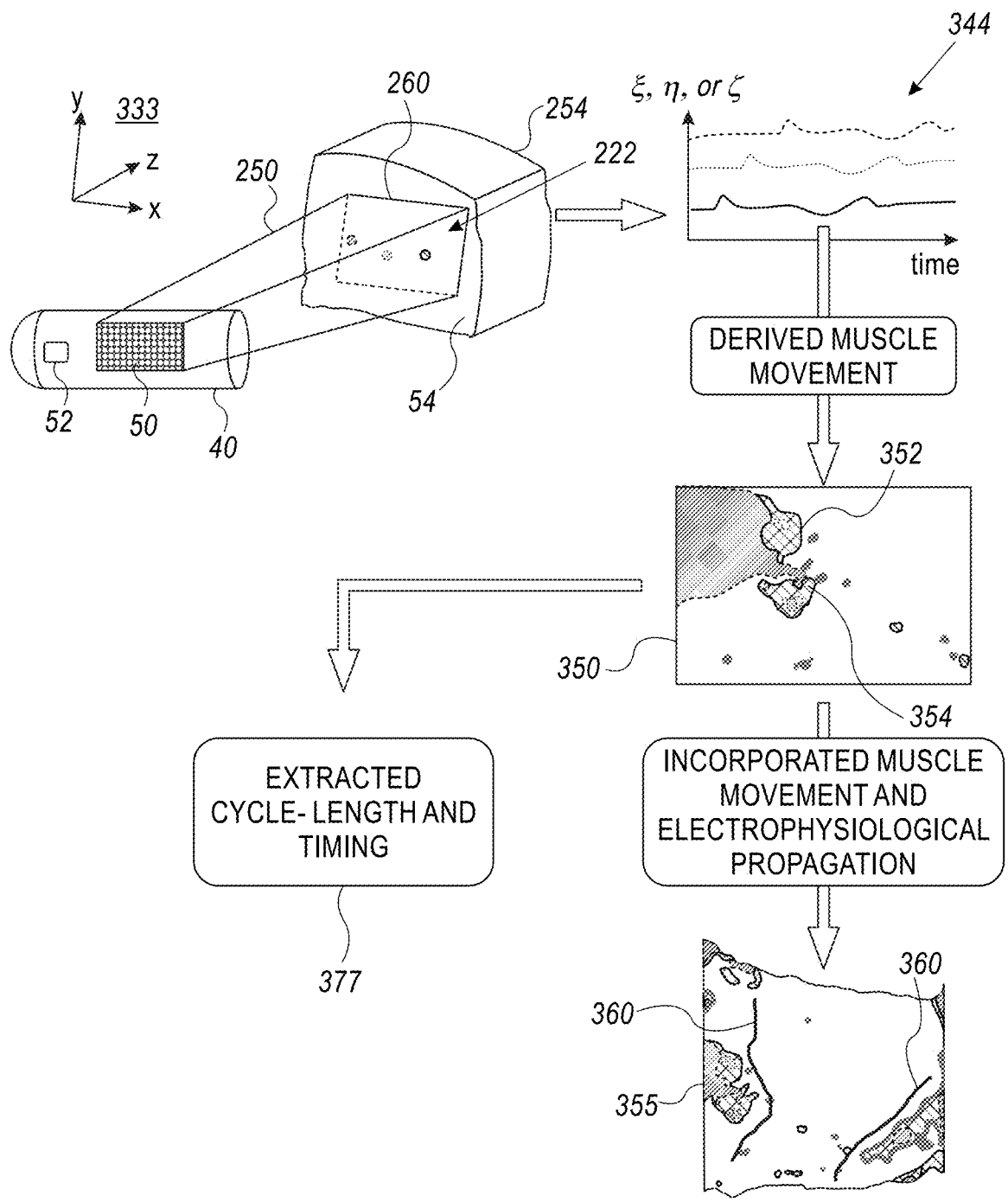
FIG. 2 is a schematic, pictorial illustration of an ultrasound intracardiac acquisition using the system of FIG. 1, followed by derivation of a tissue motion map, composite tissue motion, EP propagation map, and EP parameters, in accordance with embodiments of the present invention.

FIG. 2 is a schematic, pictorial illustration of an ultrasound intracardiac acquisition using system 20 of FIG. 1, followed by derivation of tissue motion map 350, composite tissue motion, local activation time (LAT) map 355, and EP parameters 377, in accordance with embodiments of the present invention.

As seen, system 20 performs ultrasound 2D beam 250 acquisition of an imaged section 260 of inner wall 54 of an organ 254 using catheter 21. During ultrasound acquisition, location sensor 52 tracks the position, direction, and orientation of ultrasound array 50 in a coordinate system 333 of the magnetic tracking system of FIG. 1.

FIG. 2 further shows how particular tissue locations, $\{(\xi_j, \eta_j, \zeta_j)\}$ 222 in wall 54 are tracked in three dimensions over time, yielding graphs 344 of $\{(\xi_j(t), \eta_j(t), \zeta_j(t))\}$.

Using the tracked locations in 3D, and equations 1 and 2 above, processor 39 generates a rendering 350 of tissue strain. Rendering 350 can be a color-coded rendering, where different colors 352 indicate different levels of strain. In rendering 350, a scar tissue region 354 can be identified by its unique color to indicate very low strain (e.g., a strain below a given threshold).

As seen in FIG. 2, using registration, enabled by sensor 52 readings of array 50 location, processor 39 may further combine rendering 350 with a rendering of an EP property (such as rendering of LAT values) to obtain composite rendering 355. As seen, both EP wavefronts 360 and the color-coded physical motion of rendering 350 are observed on the same map 355 at the same time.

Finally, processor 39 can analyze map 350 to derive and show parameters 377 of the heart beating, such as the cycle length and the timing of the beats.

The example configuration shown in FIG. 2 is chosen purely for the sake of conceptual clarity. For example, composite map 355 may comprise other EP maps such as a bipolar tissue-voltage level or unipolar tissue-voltage level maps.

Figure 3:
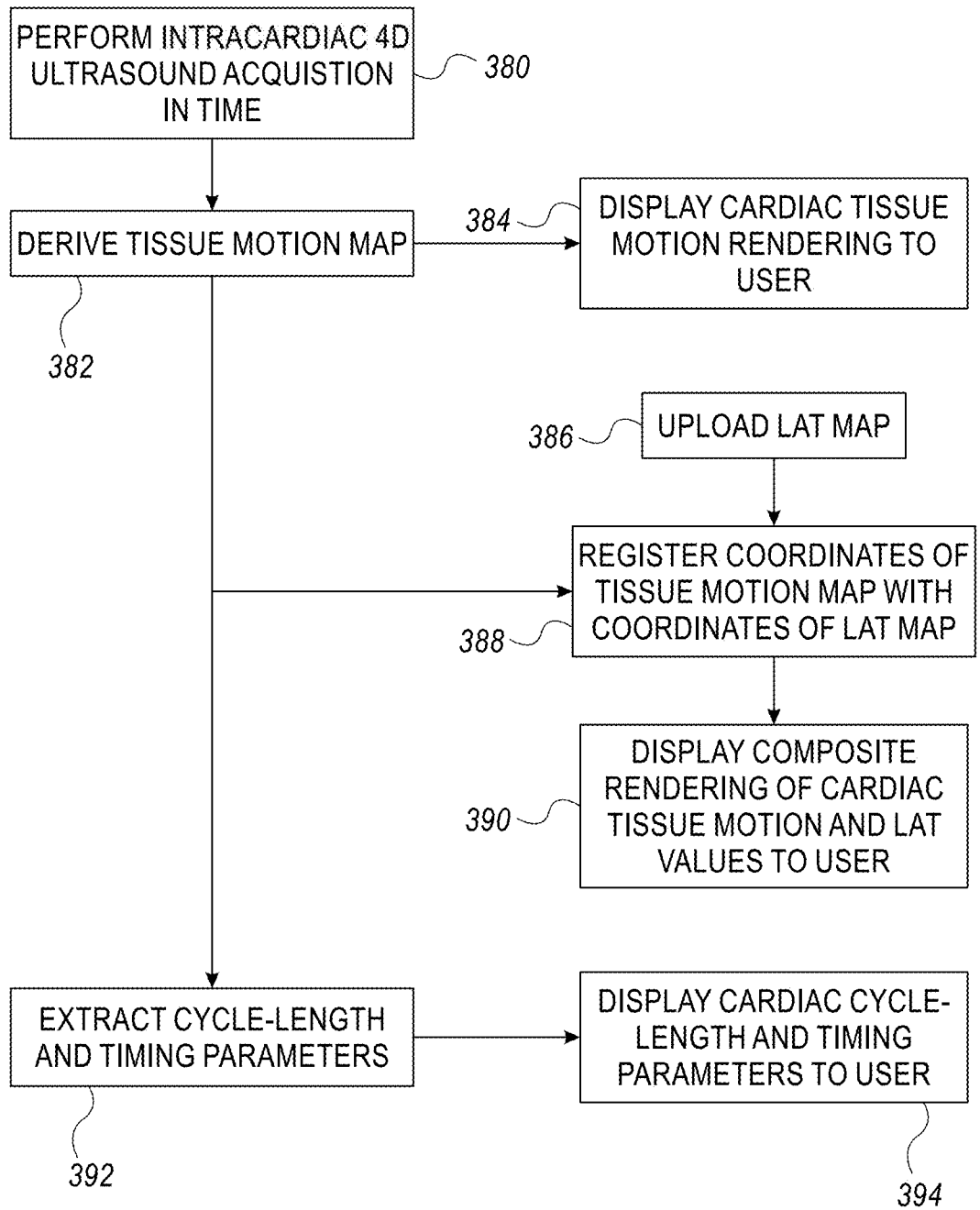
FIG. 3 is a flow chart that schematically illustrates a method for deriving and displaying the results of FIG. 2, in accordance with an embodiment of the present invention.

FIG. 3 is a flow chart that schematically illustrates a method for deriving and displaying the results of FIG. 2, in accordance with an embodiment of the present invention. The procedure begins by performing an ultrasound 2D acquisition inside a cardiac chamber, such as shown in FIG. 1, at a 4D ultrasound acquisition step 380.

Next, at a tissue motion map derivation step 382, processor 39 derives a tissue motion map, such as rendering 350 described in FIG. 2.

At a 3D strain rendering presentation step 384, processor 39 displays the cardiac tissue motion rendering of step 382 to a user, such as shown with rendering 55 on monitor 27 of FIG. 1.

To produce a composite map, such as map 360, processor 39 registers, using readings from sensor 52, coordinates of a tissue motion map with coordinates of an EP map, such as of a LAT map, at a coordinate registration step 388.

Subsequently, processor 39 can display the composite rendering of step 388 to a user on monitor 27 of FIG. 1, at a composite rendering presentation step 390.

Using the strain map derived in step 382, processor 39 extracts cardiac functioning parameters, such as parameters 377 of the heart beating of FIG. 2, at cardiac parameters extraction step 392. Finally, processor 39 can display the cardiac parameters extracted from a motion map of step 382 to a user on monitor 27 of FIG. 1, at cardiac parameters presentation step 394. In an embodiment, the cardiac parameters (e.g., cycle time) are displayed as a graphically-encoded a 3D rendering. Additionally or alternatively, the cardiac cycle timing can be used as a trigger signal for synchronizing some external device.

In various embodiments, the processes of FIG. 3 above can be applied to 4D images and/or to 3D images, as appropriate.

Although the embodiments described herein mainly address cardiac applications, the methods and systems described herein can, mutatis mutandis, be used in other body organs. For example, strain information from ultrasound can be correlated with levels of calcium in the muscle estimated using another imaging modality. As another example, in assessing diaphragm functioning, ultrasound can be used for measuring the diaphragm strain with correlation to the nerve excitation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
an intracardiac ultrasound probe configured for insertion into an organ of a body, the ultrasound probe comprising:
a two-dimensional (2D) ultrasound transducer array affixed to the ultrasound probe; and
a sensor configured to output signals indicative of a position, direction and orientation of the 2D ultrasound transducer array inside the organ; and
a processor, which is configured to:
using the signals output by the sensor, register multiple ultrasound images of a tissue region, acquired over a given time duration by the 2D ultrasound transducer array, with one another;
estimate, based on the ultrasound images acquired over the given time duration, three-dimensional displacements as a function of time for one or more locations in the tissue region;
estimate respective mechanical strains of the one or more locations in the tissue region, based on the three-dimensional displacements;
estimate, based on an amount of movement associated with the three-dimensional displacements, a cardiac cycle length and a timing of the cardiac cycle wherein the cycle length and the timing of the cardiac cycle are correlated with measured ECG signals;
identify, based on the estimating of the cardiac cycle length and the timing of the cardiac cycle, an irregularity comprising at least one of atrial fibrillation and premature ventricular contraction; and
present to a user a time-dependent rendering of the mechanical strains together with an electrophysiological (EP) signal layer comprising EP propagation indicated by a plurality of EP wavefronts on a single map of the organ, wherein the EP wavefronts and the mechanical strains may be observed on the single map at the same time.

2. The medical system according to claim 1, wherein the EP signal layer comprises local activation times (LAT).

3. The medical system according to claim 1, wherein the EP signal layer comprises one of bipolar tissue-voltage levels and unipolar tissue-voltage levels.

4. The medical system according to claim 1, wherein the processor is configured to generate, using the signals output by the sensor, a composite rendering comprising a layer of timing of heart beats and a layer of local activation times (LAT).

5. The medical system according to claim 1, wherein the processor is further configured to identify scar tissue in the tissue region using the estimated strains.

6. The medical system of claim 1, wherein the processor is further configured to convert an amount of movement associated with the three-dimensional displacements into a color scale and overlaying colors indicative of the amount of movement on an ultrasound image.

7. The medical system of claim 1, wherein the processor is further configured to compute a 3D strain tensor configured to be visualized over the rendering, where the 3D strain tensor is calculated as:

$$E = \tfrac{1}{2}(F^T F - I)$$

wherein I is an identity matrix, and F is a tissue deformation gradient tensor given by:

$$F = \begin{pmatrix} \frac{\partial \xi}{\partial x} & \frac{\partial \xi}{\partial y} & \frac{\partial \xi}{\partial z} \\ \frac{\partial \eta}{\partial x} & \frac{\partial \eta}{\partial y} & \frac{\partial \eta}{\partial z} \\ \frac{\partial \zeta}{\partial x} & \frac{\partial \zeta}{\partial y} & \frac{\partial \zeta}{\partial z} \end{pmatrix}$$

where $\xi$, $\eta$ and $\zeta$ represent components at a measurement time and x, y, and z represent mutually orthogonal components at the reference time.

8. A method, comprising:
inserting an intracardiac ultrasound probe into an organ of a body, the ultrasound probe comprising:
- a two-dimensional (2D) ultrasound transducer array affixed to the ultrasound probe; and
- a sensor configured to output signals indicative of a position, direction and orientation of the 2D ultrasound transducer array inside the organ;

using the signals output by the sensor, registering multiple ultrasound images of a tissue region, acquired over a given time duration by the 2D ultrasound transducer array, with one another;

estimating, based on the ultrasound images acquired over the given time duration, three-dimensional displacements as a function of time for one or more locations in the tissue region;

estimating respective mechanical strains of the one or more locations in the tissue region, based on the three-dimensional displacements;

estimating, based on an amount of movement associated with the three-dimensional displacements, a cardiac cycle length and a timing of the cardiac cycle wherein the cycle length and the timing of the cardiac cycle are correlated with measured ECG signals;

identifying, based on the estimating of the cardiac cycle length and the timing of the cardiac cycle, an irregularity comprising at least one of atrial fibrillation and premature ventricular contraction; and presenting to a user a time-dependent rendering of the mechanical strains together with an electrophysiological (EP) signal layer comprising EP propagation indicated by a plurality of EP wavefronts on a single map of the organ, wherein the EP wavefronts and the mechanical strains may be observed on the single map at the same time.

9. The method according to claim 8, wherein the EP signal layer comprises local activation times (LAT).

10. The method according to claim 8, wherein the EP signal layer comprises one of bipolar tissue-voltage levels and unipolar tissue-voltage levels.

11. The method according to claim 8, further comprising generating, using the signals output by the sensor, a composite rendering comprising a layer of timing of heart beats and a layer of local activation times (LAT).

12. The method according to claim 8, further comprising identifying scar tissue in the tissue region using the estimated strains.

13. The method of claim 8, further comprising the step of converting an amount of movement associated with the three-dimensional displacements into a color scale and overlaying colors indicative of the amount of movement on an ultrasound image.

14. The method of claim 8, further comprising the step of computing a 3D strain tensor configured to be visualized over the rendering, where the 3D strain tensor is calculated as:

$$E = \tfrac{1}{2}(F^T F - I)$$

wherein I is an identity matrix, and F is a tissue deformation gradient tensor given by:

$$F = \begin{pmatrix} \dfrac{\partial \xi}{\partial x} & \dfrac{\partial \xi}{\partial y} & \dfrac{\partial \xi}{\partial z} \\ \dfrac{\partial \eta}{\partial x} & \dfrac{\partial \eta}{\partial y} & \dfrac{\partial \eta}{\partial z} \\ \dfrac{\partial \zeta}{\partial x} & \dfrac{\partial \zeta}{\partial y} & \dfrac{\partial \zeta}{\partial z} \end{pmatrix}$$

where $\xi$, $\eta$ and $\zeta$ represent components at a measurement time and x, y, and z represent mutually orthogonal components at the reference time.

* * * * *